United States Patent
Lemole

[11] Patent Number: 5,824,069
[45] Date of Patent: Oct. 20, 1998

[54] PROSTHETIC HEART VALVE WITH SUTURING MEMBER HAVING NON-UNIFORM RADIAL WIDTH

[75] Inventor: Gerald M. Lemole, Huntingdon Valley, Pa.

[73] Assignee: Medtronic, Inc., Minneapolis, Minn.

[21] Appl. No.: 967,349

[22] Filed: Oct. 27, 1997

Related U.S. Application Data

[63] Continuation of Ser. No. 712,395, Sep. 13, 1996, abandoned.

[51] Int. Cl.⁶ ...................................................... A61F 2/24
[52] U.S. Cl. .................................................................. 623/2
[58] Field of Search ...................................................... 623/2

[56] References Cited

U.S. PATENT DOCUMENTS

| | | |
|---|---|---|
| 3,513,485 | 5/1970 | Davila . |
| 3,723,996 | 4/1973 | Raible et al. . |
| 3,727,240 | 4/1973 | Child . |
| 3,737,919 | 6/1973 | Child . |
| 3,763,548 | 10/1973 | Anderson . |
| 3,781,969 | 1/1974 | Anderson . |
| 3,800,403 | 4/1974 | Anderson et al. . |
| 3,812,542 | 5/1974 | Shiley . |
| 3,825,956 | 7/1974 | Child . |
| 3,825,957 | 7/1974 | Kaster . |
| 3,835,475 | 9/1974 | Child . |
| 3,858,246 | 1/1975 | Milo . |
| 3,859,668 | 1/1975 | Anderson . |
| 3,903,548 | 9/1975 | Nakib . |
| 3,953,898 | 5/1976 | Bloch . |
| 3,959,827 | 6/1976 | Kaster . |
| 3,966,401 | 6/1976 | Hancock et al. . |
| 3,996,623 | 12/1976 | Kaster . |
| 4,021,863 | 5/1977 | Woien . |
| 4,035,849 | 7/1977 | Angell et al. ............................... 623/2 |
| 4,050,893 | 9/1977 | Hancock et al. . |
| 4,057,857 | 11/1977 | Fettel . |
| 4,078,268 | 3/1978 | Possis . |
| 4,084,268 | 4/1978 | Ionescu et al. . |
| 4,106,129 | 8/1978 | Carpentier et al. . |
| 4,172,295 | 10/1979 | Batten . |
| 4,259,753 | 4/1981 | Liotta et al. ......................... 623/900 X |
| 4,306,319 | 12/1981 | Kaster . |
| 4,339,831 | 7/1982 | Johnson . |
| 4,364,126 | 12/1982 | Rosen et al. . |
| 4,366,581 | 1/1983 | Shah ............................................ 623/2 |
| 4,372,743 | 2/1983 | Lane . |

(List continued on next page.)

FOREIGN PATENT DOCUMENTS

| | | | |
|---|---|---|---|
| 9119465 | 12/1991 | WIPO ....................................... 623/2 |
| WO 94/07437 | 4/1994 | WIPO . |

OTHER PUBLICATIONS

Cartwright, R.S., et al., vol. X Trans. Amer. Soc. Artif. Int. Organs, 1964, pp. 231–236.

*Primary Examiner*—David H. Willse
*Attorney, Agent, or Firm*—Baker, Maxham, Jester & Meador

[57] ABSTRACT

A prosthetic heart valve, either of the mechanical type, or the bioprosthetic type, comprises a circular frame element, a check valve element and a suturing member surrounding the circular frame element. The circular frame element defines a circular opening for the passage of blood therethrough. The check valve element is connected to, and extends across, the circular frame element and is configured to substantially permit the flow of blood through the circular opening in a first direction and to substantially impair the flow of blood through the circular opening in a second direction opposite the first direction. The suturing member surrounds the circular frame element and has a first radial width in a first circumferential region substantially greater than a second radial width in a second circumferential region to define an extended portion of the suturing member. The extended portion of the suturing member can be attached to a downwardly sagging portion of a patient's valve annulus with sutures, thereby ensuring proper orientation of the valve in the patient's heart.

21 Claims, 3 Drawing Sheets

U.S. PATENT DOCUMENTS

| | | |
|---|---|---|
| 4,443,895 | 4/1984 | Lane . |
| 4,576,605 | 3/1986 | Kaidash et al. .............................. 623/2 |
| 4,629,459 | 12/1986 | Ionescu et al. . |
| 4,692,164 | 9/1987 | Dzemeshkevich et al. . |
| 4,816,029 | 3/1989 | Penny, III et al. . |
| 4,822,355 | 4/1989 | Bhuvaneshwar . |
| 4,935,030 | 6/1990 | Alonso . |
| 5,080,669 | 1/1992 | Tascon et al. . |
| 5,163,953 | 11/1992 | Vince . |
| 5,175,187 | 12/1992 | Baligadoo . |
| 5,178,633 | 1/1993 | Peters . |
| 5,192,309 | 3/1993 | Stupka et al. . |
| 5,192,313 | 3/1993 | Budd et al. . |
| 5,258,021 | 11/1993 | Duran . |
| 5,306,296 | 4/1994 | Wright et al. . |
| 5,314,467 | 5/1994 | Shu . |
| 5,352,240 | 10/1994 | Ross . |
| 5,376,112 | 12/1994 | Duran . |
| 5,397,348 | 3/1995 | Campbell et al. . |
| 5,489,297 | 2/1996 | Duran . |

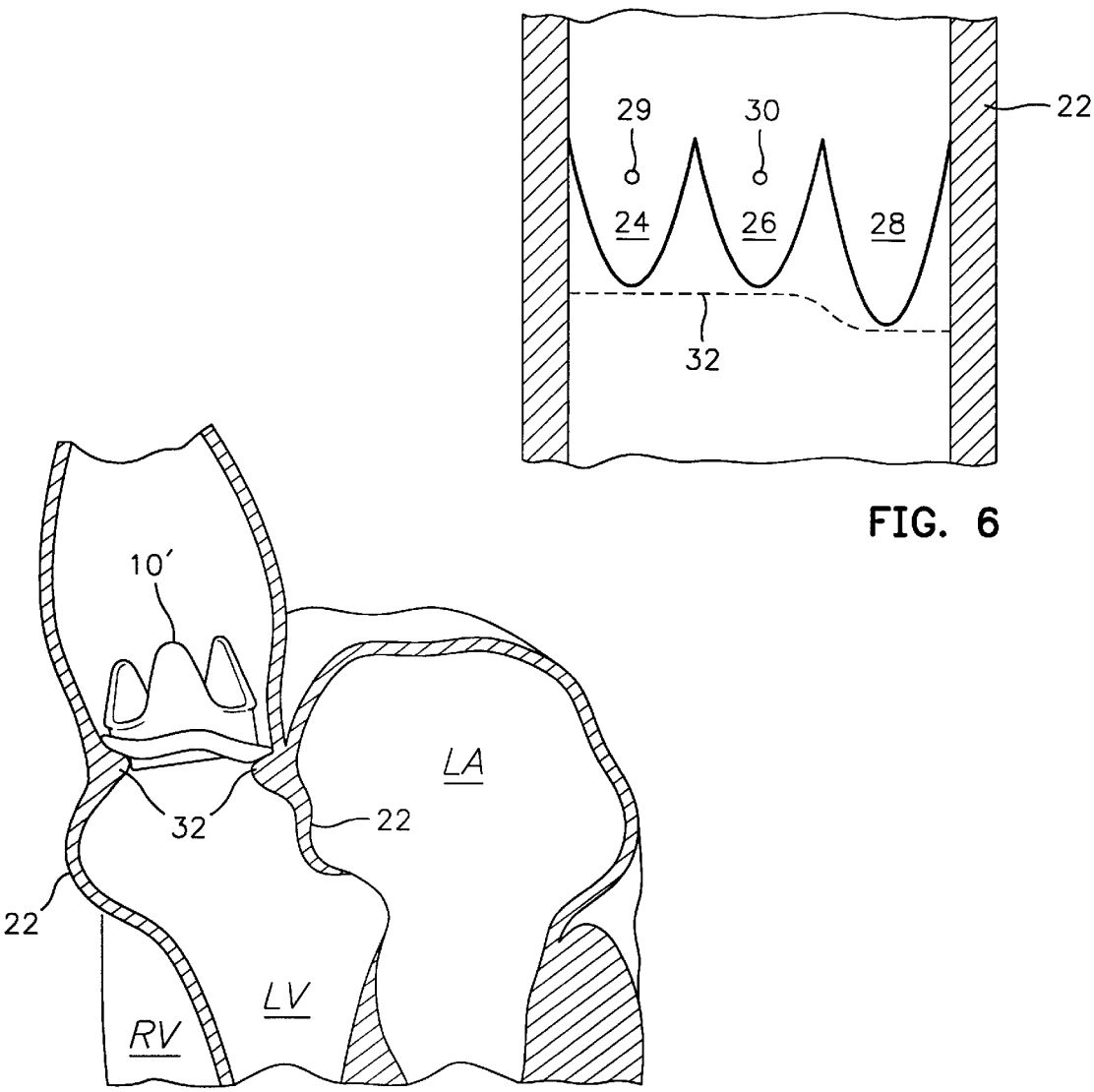
FIG. 6
FIG. 7
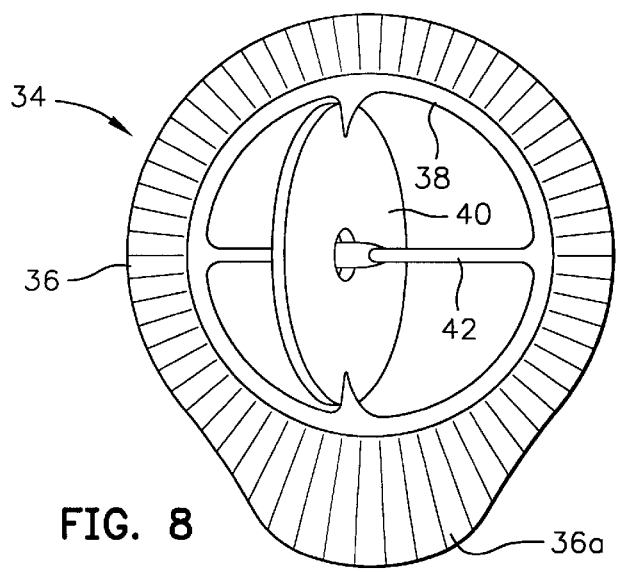
FIG. 8

PROSTHETIC HEART VALVE WITH SUTURING MEMBER HAVING NON-UNIFORM RADIAL WIDTH

This application is a continuation of application Ser. No. 08/712,395, filed Sep. 13, 1996, now abandoned.

BACKGROUND OF THE INVENTION

The present invention relates to surgical implants, and more particularly, to prosthetic heart valves.

In many individuals, one or more heart valves may not function normally. This may be the result of disease, degeneration or a congenital defect. In the case of the aortic valve, dysfunction can result from a narrowing of the valve orifice (stenosis), or from valve incompetence, such that the valve does not fully open or close. Severe heart valve dysfunction is life threatening.

For well over thirty years, severe heart valve dysfunction has been treated by replacing the valve with a mechanical prosthetic valve, or alternatively, with a bioprosthetic valve. A mechanical heart valve comprises a ridged circular ring with a flapper element made of a rigid material, for example, pyrolitic carbon. The hydrodynamic characteristics of a mechanical heart valve require the patient to be on a carefully monitored dose of anticoagulants. A bioprosthetic heart valve typically comprises a semi-rigid plastic stent that supports a tissue valve. Xenografts are commonly used in bioprosthetic heart valves, particularly the porcine aortic valve, since it is similar in anatomy to the human aortic valve (both being tricuspid) and is readily available in a variety of sizes. Patients receiving bioprosthetic heart valve implants need not take anticoagulant drugs. In addition, the porcine aortic xenograft is treated with glutaraldehyde to preserve the tissue and minimize antigenic reactions in the patient.

Both the mechanical heart valve and the bioprosthetic heart valve have a suturing ring to allow the surgeon to precisely anchor the valve in position, in, for example, the aortic annulus. Typically, the suturing ring comprises a circular fabric structure surrounding the metal seat of the mechanical heart valve or the fabric covered stent of the bio-prosthetic heart valve. Usually the lead cardiac surgeon stitches polypropylene or other suture material through the tissue at the annulus where the patient's native heart valve has been surgically removed. Each suture is drawn through the fabric suturing ring of the prosthetic heart valve which is held by an assistant away from the heart. When all of the sutures have been made, and passed through the suturing ring around its circumference, the heart valve is slid down into position. Each suture is then tied down. Care must be taken to ensure that the rotational orientation of the valve is appropriate in order to optimize the hydrodynamic performance of the implant. Many patients undergoing replacement of their aortic heart valves exhibit a downward sagging of the non-coronary portion of the aortic annulus. Prosthetic heart valves which have heretofore been developed have all included suturing rings having a uniform or constant radial width. As a result, when installed in a patient having a downwardly sagging, non-coronary portion of the aortic annulus, such valves may end up tilted relative to the preferred axis. This has three undesirable effects. First of all, the prosthetic heart valve may not exhibit its optimum hydrodynamic characteristics. Second, in the case of a bioprosthetic heart valve having a plastic stent, the legs of the stent may protrude into the surrounding tissue, resulting in stress on the tissue, particularly during valve closure. Third, the tilted orientation of the heart valve implant may lead to a difficult closure of the aortotomy. In addition, in the case of an aortic heart valve replacement, a tilted implant can have negative effects on the overall functioning of the heart, since the anterior leaflet of the mitril valve is in close proximity, and effectively an extension of, the non-coronary cusp or leaflet of the aortic valve. A heart valve implanted into the aortic valve where the annulus has sagged can pull up on the anterior leaflet of the mitril valve, distorting its function and operation.

SUMMARY OF THE INVENTION

Accordingly, it is the primary object of the present invention to provide an improved prosthetic heart valve.

It is another object of the present invention to provide an improved suturing member for a prosthetic heart valve.

In accordance with the present invention a prosthetic heart valve, either of the mechanical type, or the bioprosthetic type, comprises a circular frame element, a check valve element and a suturing member surrounding the circular frame element. The circular frame element defines a circular opening for the passage of blood therethrough. The check valve element is connected to, and extends across, the circular frame element and is configured to substantially permit the flow of blood through the circular opening in a first direction and to substantially impair the flow of blood through the circular opening in a second direction, opposite the first direction. The suturing member surrounds the circular frame element and has a first radial width in a first circumferential region substantially greater than a second radial width in a second circumferential region to define an extended portion of the suturing member. The extended portion of the suturing member can be attached to a downwardly sagging portion of a patient's valve annulus with sutures, thereby ensuring proper orientation of the valve in the patient's heart.

BRIEF DESCRIPTION OF THE DRAWINGS

FIG. 6 is a schematic illustration of the coronary and non-coronary valve cusps of the aortic valve of an elderly patient illustrating the downward sagging of the non-coronary portion of the aortic annulus.

FIG. 7 is a simplified vertical sectional view of a human heart illustrating the implantation of the bioprosthetic heart valve of FIG. 5.

FIG. 8 is a top plan view of a mechanical heart valve embodying the present invention.

DETAILED DESCRIPTION OF THE PREFERRED EMBODIMENTS

Referring to FIGS. 1–4, a bioprosthetic heart valve 10 includes a circular frame element in the form of a stent 12

Figure 2:
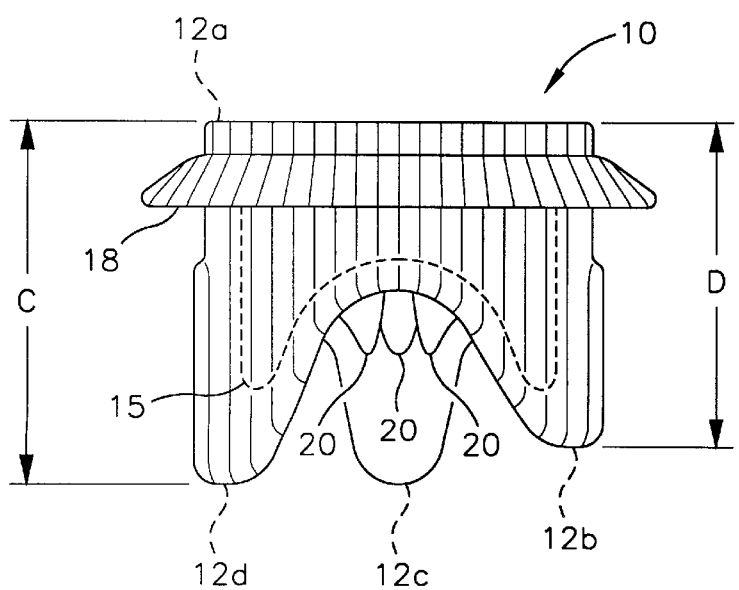
FIG. 2 is a side elevation view of the bioprostheic heart valve of FIG. 1.
Figure 3:
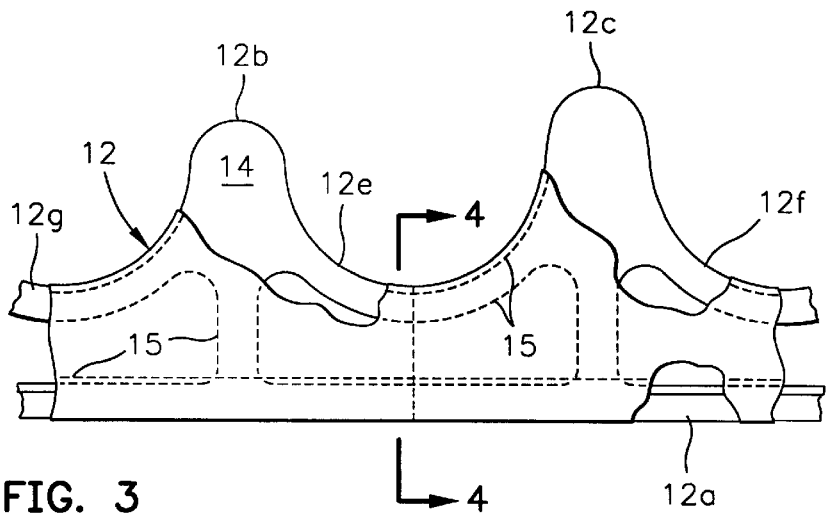
FIG. 3 is a greatly enlarged, fragmentary, diagrammatic side elevation view of the bioprosthetic heart valve of FIGS. 1 and 2. The heart valve has been sliced and unwrapped to a flat configuration and the suturing member is not illustrated for the sake of clarity.

(FIG. 3). The stent 12 includes a ring portion 12a and three circumferentially spaced posts which extend generally orthogonal to the plane of ring portion 12a. Only two of the posts 12b and 12c are visible in FIG. 3. The third post 12d is visible in FIG. 2.

The ring portion 12a (FIG. 3) of the stent 12 defines a circular opening for the passage of blood therethrough. The stent 12 is preferably made of a semi-rigid plastic material such as polypropylene, acetal co-polymer or homo-polymer. Such materials are commercially available from, for example, American Celanese Corporation. During implantation of the bioprosthetic heart valve 10, a ratchet mechanism is utilized, according to well known techniques, to inwardly deflect the stent posts 12b, 12c and 12d for ease of insertion into the patient's native valve annulus. Later the stent posts are allowed to resume their normal positions exemplified in FIG. 2 to help anchor the prosthetic valve 10 in position.

Figure 4:
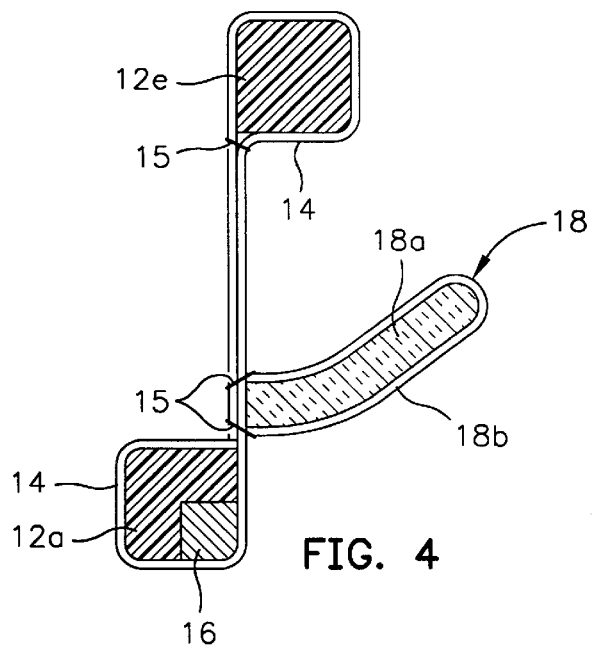
FIG. 4 is a vertical sectional view of the bioprosthetic heart valve of FIGS. 1 and 2 taken along line 4—4 of FIG. 3. In this figure, the suturing member has been added to show its relationship to the other structure of the bioprosthetic heart valve.

Referring to FIG. 2, two of the stent posts 12c and 12d are longer than the third stent post 12b. The stent posts 12b, 12c and 12d are connected by arcuate arms 12e, 12f and 12g (FIG. 3). It will be understood that the ring portion 12a, the stent posts 12b, 12c and 12d, and the arm portions 12e, 12f, and 12g can all be integrally molded out of the aforementioned plastic material. The stent 12 is covered in its entirety with a bio-compatible fabric such as woven polyester 14 (FIG. 3). The fabric 14 is secured to the stent 12 by stitching 15. One suitable polyester fabric is sold under the trademark DACRON by DuPont. As shown in FIG. 4, the ring portion 12a of the plastic stent 12 is formed with an annular recess in which a polished metal stiffening ring 16 is seated.

The bioprosthetic heart valve 10 further includes a radially extending suturing member 18 (FIGS. 1 and 2) which is not illustrated in FIG. 3. The suturing member 18 is generally pear-shaped. Referring to FIG. 4, the suturing member 18 includes an inner felt ring 18a and an outer biocompatible fabric covering 18b which may also be made of the same polyester fabric material as the material 14 that covers the plastic stent 12. The suturing member 18 is also preferably provided with a pair of colored markings 18d and 18e which are utilized by the surgeon in fixing the proper rotational alignment of the heart valve 10 inside the patient's native valve. Stitching 15 also holds the fabric covering 18b to the ring 18a and to the covering 14 over the stent 12.

A check valve element in the form of a porcine aortic valve 20 (FIGS. 1 and 2) is connected to, and extends across the circular opening defined by the ring portion 12a of the plastic stent 12 and its fabric covering 14. The porcine aortic valve 20 is trileaflet. i.e. tricuspid, and is readily available in a variety of sizes to match the inner diameter of the circular opening formed by the covered stent 12. The porcine aortic valve 20 is first treated with an agent, such as glutaraldehyde, to fix the valve tissue, sterilize it, and decrease its antigenicity, as is well known in the art. The periphery of the porcine valve 20 is sutured to the fabric 14 covering the ring portion 12a of the stent 12, as is well known in the art. Further details of various materials, and techniques for constructing the bioprosthetic valve 10 may be obtained from U.S. Pat. No. 5,306,296 of John T. M. Writ, et al. assigned to Medtronic, Inc.; U.S. Pat. No. 3,781,969 of Lawrence Anderson assigned to Medical Incorporated; U.S. Pat. No. 3,859,668 of Lawrence Anderson assigned to Medical Incorporated; and U.S. Pat. No. 5,178,633 of T. Scott Peters assigned Carbon Implants, Inc., the entire disclosures of which are hereby incorporated by reference.

Figure 1:
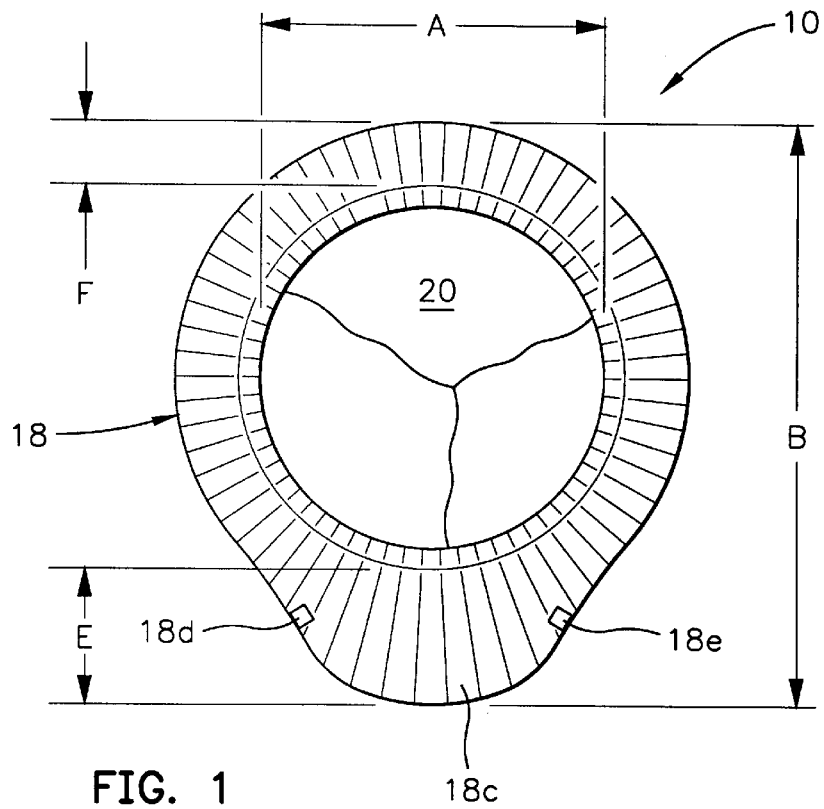
FIG. 1 is a top plan view of a bioprosthetic heart valve embodying the present invention.

Referring to FIG. 1, the suturing member 18 has a first radial width F in a first circumferential region comprising approximately three-quarters of the way around the stent 12, and a second radial width E in a second circumferential region comprising approximately one-quarter the way around the stent 12. The second radial width E is substantially greater than the first radial width F defining an extended portion 18c of the suturing member 18. The extended portion 18c of the suturing member 18 is utilized for attachment of the prosthetic heart valve 10 to a downwardly sagging portion of a patient's native valve annulus utilizing sutures. By way of example, the radial width of the extended portion 18c of the suturing member 18 is preferably between about 1¼ and 3½ times the radial width of the remaining portion of the suturing member 18.

It will be understood by those skilled in the art that the so-called annulus diameter A in FIG. 1 is sized in accordance with the diameter of the native valve annulus in the patient's heart into which the prosthetic valve 10 is to be implanted. Similarly, the conventional bioprosthetic heart valve (not illustrated) has a suturing member whose radial width is uniform throughout the circumference of the valve and which bears a proportional relationship to the annulus diameter A. I have found that in many patients, frequently those who are elderly, and most often in the aortic valve chamber, the valve annulus sags downwardly in the non-coronary cusp.

Figure 5:
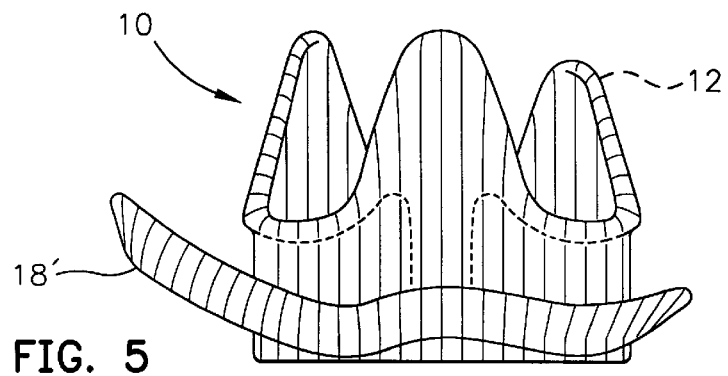
FIG. 5 is a side elevation view of another bioprosthetic heart valve embodying the present invention in which the suturing member has a scalloped configuration.

FIG. 5 illustrates an alternate embodiment of the bioprosthetic heart valve 10' which is similar in all respects to the bioprosthetic heart valve 10 of FIGS. 1–4 except that its suturing member 18' has a scalloped configuration that is particularly suited for implantation into the native aortic valve annulus.

Referring to FIG. 6, the aortic valve walls are illustrated schematically as a pair of parallel vertical lines 22. The right and left aortic valve cuspids 24 and 26 and the non-coronary cuspid 28 are shown between the walls 22. The cuspids 24 and 26 have coronary ostium 29 and 30, respectively. The non-coronary cuspid 28 is illustrated somewhat downwardly extended. The corresponding downward sagging of the aortic annulus is illustrated by the phantom line 32 extending at a first level below the right and left coronary cuspids 24 and 26 and then descending below the non-coronary cuspid 28.

Table I set out below gives representative examples the dimensions of the bioprosthetic heart valve 10:

TABLE I

| SIZE (mm) | A | B | C | D | E | F |
| --- | --- | --- | --- | --- | --- | --- |
| 19 | 16.0 | 30 | 16 | 14 | 8.2 | 2.5 |
| 21 | 18.0 | 33 | 17 | 15 | 10 | 3.5 |
| 23 | 20.0 | 36 | 18 | 16 | 11.8 | 4.5 |

The dimensions A, B, C, D, E and F of Table I are labeled in FIGS. 1 and 2.

Referring to FIG. 7, the bioprosthetic heart valve 10' of FIG. 5 is shown installed into the native aortic vessel with the extended portion 18c of its suturing member 18 sewn to the root wall 22. Thus, the axis of the prosthetic heart valve 10', which extends orthogonally through the ring portion 12a of the stent 12, is properly oriented to ensure optimum hydrodynamic performance of the valve. If the extended portion 18c of the suturing member 18 were not available, and if the suturing member had only a uniform radial width F around its entire circumference, it would be necessary to slightly tilt the valve 10' and/or pull up on the mitral leaflet toward the aortic valve. Such a tilted orientation of a bioprosthetic valve with a conventional suturing member might also push one of the covered stent posts 12b, 12c, or 12d into the wall 22, resulting in trauma to the same. Furthermore, such a protrusion of one of the stent posts could make it difficult for the surgeon to close the aortotomy. Heart valves with my extended suturing member may be utilized regardless of whether or not the native valve annulus of the patient exhibits sagging.

Referring to FIG. 8, a mechanical heart valve 34 may also be provided with a suturing member 36 having an extended portion 36a. The extended portion 36a of the suturing flange of the mechanical heart valve 34 serves the same function as the extended portion 18c of the suturing member 18 of the bioprosthetic heart valves 10 and 10'. The construction of the mechanical heart valve 34 is otherwise conventional. The circular frame element that defines the circular opening for the passage of blood takes the form of a metal or pyrolytic carbon ring 38. A mechanical flapper valve 40, which may also be made of pyrolytic carbon, is pivotally mounted on the end of an arm 42 which extends diametrically from the inner periphery of the ring 38. As is the case in conventional mechanical heart valves, the suturing member 36 may be rotated relative to the ring 38 for proper orientation of the mechanical flapper valve 40 in the patient's native valve annulus.

Having described various embodiments of my improved prosthetic heart valve with a suturing member having an extended portion, it will be understood that my invention may be modified in both arrangement and detail. Therefore, the protection afforded my invention should only be limited in accordance with the scope of the following claims.

I claim:

1. A prosthetic heart valve, comprising:
a circular frame element defining an opening for the passage of blood;
a check valve element connected to the circular frame element and configured to substantially permit the flow of blood through the opening in a first direction and to substantially impair the flow of blood through the opening in a second direction opposite the first direction; and
a suturing member surrounding the circular frame element and having a first radial width in a first circumferential region of about one-quarter the circumference substantially greater than a second substantially uniform radical width in a second remainder of the circumferential region to define an extended portion for attachment to a downwardly sagging portion of a patient's valve annulus.

2. A prosthetic heart valve according to claim 1 wherein the check valve element is a mechanical flapper valve.

3. A prosthetic heart valve according to claim 1 wherein the check valve element includes a xenograft.

4. A prosthetic heart valve according to claim 1 wherein the circular frame element comprises a plastic stent.

5. A prosthetic heart valve according to claim 1 wherein the circular frame element comprises a pyrolytic carbon ring.

6. A prosthetic heart valve according to claim 2 wherein the flapper valve is made of pyrolytic carbon.

7. A prosthetic heart valve according to claim 1 wherein the suturing member is a radially extending flange.

8. A prosthetic heart valve according to claim 7 wherein the flange is scalloped.

9. A prosthetic heart valve according to claim 1 wherein the suturing member includes a bio-compatible fabric.

10. A prosthetic heart valve according to claim 1 wherein the first radial width is between about one and one-quarter and three and one-half times the second radial width.

11. A prosthetic valve, comprising:
a circular frame element defining an opening for the passage of blood therethrough;
a check valve element connected to the circular frame element and extending across the opening; and
suturing member surrounding the circular frame element and having a first radial width in a first circumferential region of about one-quarter of the circumference substantially greater than a second radial width in a second remainder of the circumferential region to define a single extended portion for attachment to a patient's valve annulus.

12. A prosthetic heart valve according to claim 1 wherein the check valve element is a mechanical flapper valve.

13. A prosthetic heart valve according to claim 1 wherein the check valve element includes a xenograft.

14. A prosthetic heart valve according to claim 11 wherein the first radial width is between about one and one-quarter and three and one-half times the second radial width.

15. A prosthetic heart valve according to claim 11 wherein the suturing member is a radially extending flange.

16. A prosthetic heart valve according to claim 15 wherein the flange is scalloped.

17. A prosthetic heart valve according to claim 11 wherein the suturing member includes a bio-compatible fabric.

18. A prosthetic heart valve according to claim 11 wherein the check valve element is a porcine aortic valve.

19. A method of securing a prosthetic heart valve in the native valve annulus of a patient's heart wherein a portion of the valve annulus sags below a remainder of the valve annulus, and wherein the prosthetic heart valve includes a circular frame element defining an opening for the passage of blood, a check valve element connected to the circular frame element and extending across the opening, comprising the steps of:
surrounding the circular frame element with a suturing member having a non-uniform radial width to define a single extended portion of about one-quarter of the circumference of the frame; and
suturing the suturing member to the patient's native valve annulus around an entire circumference of the suturing member with the extended portion of the suturing member attached to the sagging portion of the native valve annulus.

20. A prosthetic heart valve, comprising:
a circular frame element defining an opening for the passage of blood therethrough;
a check valve element connected to the circular frame element and extending across the opening; and
a generally pear-shaped suturing member surrounding the circular frame element.

21. A prosthetic heart valve, comprising:
a circular frame element defining an opening for the passage of blood;
a check valve element connected to the circular frame element and configured to substantially permit the flow of blood through the opening in a first direction and to substantially impair the flow of blood through the opening in a second direction opposite the first direction; and
a suturing member surrounding the circular frame element and having a first radial width in a first circumferential region substantially greater than a second radial width in a second circumferential region to define an extended portion, the suturing member having transition regions between the first and second regions each having a radial width that gradually transitions between the first radial width and the second radial width.

* * * * *